United States Patent [19]

Akram et al.

[11] Patent Number: 5,230,710
[45] Date of Patent: Jul. 27, 1993

[54] SUBSTITUTED 2,6-DIAMINOTOLUENES, PROCESSES FOR THEIR PREPARATION AND COLORING AGENTS FOR KERATINIC FIBERS COMPRISING THESE COMPOUNDS

[75] Inventors: Mustafa Akram, Hamburg; Winfried Seidel, Quickborn; Wolfgang Schlenther, Hamburg, all of Fed. Rep. of Germany

[73] Assignee: Hans Schwarzkopf GmbH, Hamburg, Fed. Rep. of Germany

[21] Appl. No.: 953,053

[22] Filed: Sep. 30, 1992

[30] Foreign Application Priority Data

Oct. 1, 1991 [DE] Fed. Rep. of Germany ........ 4132615

[51] Int. Cl.$^5$ ................................................ A61K 7/13
[52] U.S. Cl. ........................................ 8/408; 8/406; 8/407; 8/409; 8/410; 8/411; 8/412; 8/423; 8/435; 424/70; 564/442
[58] Field of Search .................... 8/406, 407, 408, 409, 8/410, 411, 412, 423, 435; 424/70; 260/573; 564/442

[56] References Cited

U.S. PATENT DOCUMENTS

| | | | |
|---|---|---|---|
| 3,857,674 | 12/1974 | Forsthoff et al. | 8/416 |
| 4,092,102 | 5/1978 | Halasz et al. | 8/11 |
| 4,196,145 | 4/1980 | Halasz et al. | 260/573 |
| 4,212,645 | 7/1980 | Leon et al. | 8/406 |
| 4,361,421 | 11/1982 | Bugaut et al. | 8/416 |
| 4,395,262 | 7/1983 | Konrad et al. | 8/423 |
| 4,661,114 | 4/1987 | Konrad et al. | 8/423 |
| 4,845,294 | 7/1989 | Konrad et al. | 8/416 |
| 4,886,516 | 12/1989 | Konrad et al. | 8/408 |
| 4,997,451 | 3/1991 | Clausen et al. | 8/407 |
| 5,067,966 | 11/1991 | Mager et al. | 8/405 |

FOREIGN PATENT DOCUMENTS 2449101 4/1975 Fed. Rep. of Germany .
3137473 4/1983 Fed. Rep. of Germany .
51124194 10/1976 Japan .

*Primary Examiner*—Paul Lieberman
*Assistant Examiner*—William S. Parks
*Attorney, Agent, or Firm*—Beveridge, DeGrandi, Weilacher & Young

[57] ABSTRACT

New substituted 2,6-diaminotoluenes of the general formula I

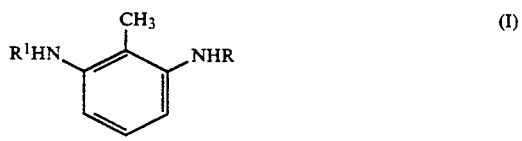

wherein R is a hydrogen atom and $R^1$ is a radical of the formula Ia $$-CH_2-CH(A)-B \qquad (Ia)$$

or R and $R^1$ are independent from each other and are represented by the formula Ia and if A in formula Ia represents a hydrogen atom, B is a hydroxyl group or HO—$CH_2$— group; if A denotes a methyl group, B is a hydroxyl group; with the proviso that formula I is not N-(2-hydroxyethyl)-2,6-toluylenediamine; processes for their preparation and coloring compositions for keratin fibers which contain them. The dyeings produced with the coloring compositions are stable, bright and intense in color. They have improved properties with respect to attack by perspiration, acid rain, detergents, sunlight, UV radiation, seawater and the like.

12 Claims, No Drawings

SUBSTITUTED 2,6-DIAMINOTOLUENES, PROCESSES FOR THEIR PREPARATION AND COLORING AGENTS FOR KERATINIC FIBERS COMPRISING THESE COMPOUNDS

BACKGROUND AND INTRODUCTION

The present invention relates to new substituted 2,6-diaminotoluene compounds of the general formula I, processes for their preparation, and coloring agents which contain these compounds for use on keratin fibers.

So-called oxidation dyes which are formed by oxidative coupling of development components (such as, for example, p-phenylenediamines, p-aminophenols or p-diaminopyridines) with coupling components (such as, for example, phenols, resorcinols, m-aminophenols, m-phenylenediamines, naphthols or pyrazolones) are of particular importance for dyeing hair. Under the conditions of use (e.g., low dyeing temperature and short dyeing time), they produce intensive colors with very good fastness properties. Oxidation dyes also play an important role in dyeing fur. Suitable oxidation dyestuff precursors must primarily meet the following prerequirements for use: during oxidative coupling of the particular coupling and development components, they must produce the desired color (which should have a good absorption and migrating capacity on hair or fur) to an adequate intensity. The dyestuffs formed must be generally stable (especially to heat) and specifically resistant to washing, light, and perspiration. In particular, they should not lead to shifts in the color of the original shade under wearing conditions. Moreover, they should be toxicologically and dermatologically acceptable.

These requirements cannot always be made to coincide. This is particularly clear in the field of so-called blue couplers. With 2,6-diaminotoluene, as the prior art, there exists a compound which on the one hand is not completely satisfactory during use because the stability of the color of the dyed hair is not satisfactory (for example, under the action of perspiration, acid rain, detergents, sunlight, UV radiation and the like), and on the other hand is also questionable from the toxicological point of view.

JP 51-124,194 A (1976) discloses the compound N-(2-hydroxyethyl)-2,6-toluylenediamine, which is caused to react with maleic anhydride to polyimide resins. DE 30 45 959 A1 describes the use of N-hydroxyalkyl-substituted m-phenylendiamines of the general formula

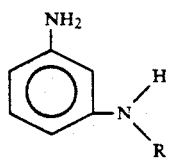

wherein R denotes a hydroxyalkyl radical with 1-4 carbon atoms and 1 or 2 hydroxyl groups as coupler component in agents for oxidative dyeing of hair to produce green to black-blue color shades. Example 4 of DE 2,449,101 1 A1 (U.S. Pat. Nos. 4,092,102 and 4,196,145) discloses the preparation of 2-hydroxyethylamino-4-aminotoluene and dyeing tests of this compound in combination with p-phenylenediamine or p-toluenediaminesulfate in agents for oxidative dyeing of hair; deep blue color shades are the result of this example. DE-3,137,473 A1 refers to 2,4-diamino-m-xylene of the general formula

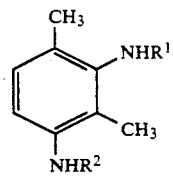

in which one of the substitutents $R^1$ or $R^2$ is a hydrogen atom and the other substituent denotes an alkyl group with 1-4 carbon atoms or a substituted alkyl group. These compounds should give, in agents for oxidative dyeing of hair, green-grey, red-brown, black-blue or dark-violet shades.

SUMMARY OF THE INVENTION

An object of the present invention is to improve the previous disadvantages of hair coloring agents on an oxidative basis. In particular, the dyeings produced on keratin fibers should be stable, bright and intense in color, and thus have significantly improved properties in respect to attack by perspiration, acid rain, detergents, sunlight, UV radiation and the like.

One object is to provide 2,6-diaminotoluene derivatives of the formula I and its salts with inorganic and organic acids

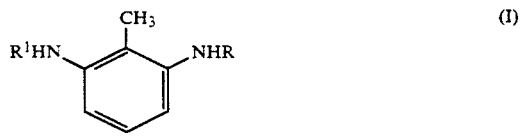

wherein R is a hydrogen atom and $R^1$ is a radical of the formula Ia

or R and $R^1$ are independent from each other and are represented by the formula Ia and if A in formula Ia represents a hydrogen atom, B is a hydroxyl group or $HO-CH_2-$ group; or if A denotes a methyl group, B is a hydroxyl group; with the proviso that formula I is not N-(2-hydroxyethyl)-2,6-toluylenediamine. The 2,6-diaminotoluene derivative is preferably 2,6-bis(2-hydroxyethylamino)-toluene or 2,6-bis(3-hydroxypropylamino)-toluene.

Another object is to provide a process for the preparation of a compound of the formula I' and its salts with inorganic and organic acids

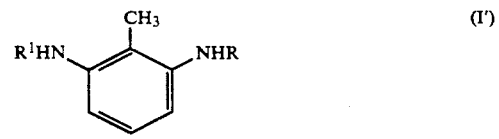

wherein R is a hydrogen atom and $R^1$ is a radical of the formula Ia

or R and $R^1$ are independent from each other and are represented by the formula Ia and if A in this formula represents a hydrogen atom, B is a hydroxyl group or HO—CH$_2$— group; or if A denotes a methyl group, B is a hydroxyl group; said process involving (a) reacting 2,6-diaminotoluene with about twice the molar amount of a chloroformic acid alkyl ester of the formula Cl—COO—CH(X)—CH$_2$—Y, wherein X=H, Y=Cl or X=CH$_3$, Y=Cl or X=H, Y=CH$_2$Cl, to give a carbamate of the formula II

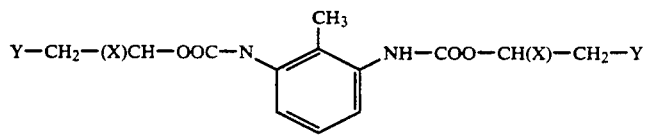 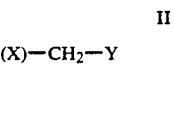

wherein X and Y have the meanings given, and converting said carbamates of the formula II, in a second stage, into a compound of the formula I', wherein R and R$^1$ denote a radical of the formula Ia, wherein A and B have the meanings already given, by treatment with a base, or (b) reacting 2-nitro-6-aminotoluene with an approximately equimolar amount of a chloroformic acid alkyl ester of the formula Cl—COO—CH(X)—CH$_2$—Y, wherein X and Y have the meanings already given, to give a carbamate of the formula III

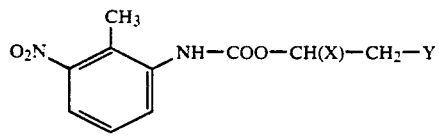

wherein X and Y have the meanings given, and converting said carbamate of the formula III, in a second stage, into a compound of the formula IV

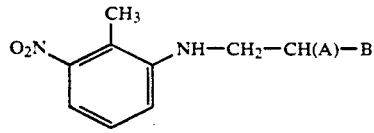

wherein A and B have the meanings given above, by treatment with a base, and subjecting said compound of the formula IV to reduction, in a third stage; and if appropriate the resulting compounds of the formula I', wherein one of R or R$^1$ denotes a hydrogen atom or R and/or R$^1$ denotes a radical of the formula Ia

and if A in this formula represents a hydrogen atom, B is a hydroxyl group or the HO—CH$_2$— group; or if A denotes a methyl group, B is a hydroxyl group, are converted into their salts with an organic or inorganic acid.

Then another object is to provide a composition for oxidative dyeing of hair containing at least one diaminotoluene derivative of the formula I' as the coupler component and a developer component therewith, said coupler being present in a sufficient amount to dye hair.

Finally, a method is provided for oxidative dyeing of hair which involves (a) mixing the composition described above with an oxidizing agent to form a mixture, and (b) applying said mixture to hair.

DETAILED DESCRIPTION OF THE INVENTION

The compounds of the general formula I' which are particularly suitable as coupler components for oxidative dyeing, meet the above-mentioned requirements to a high degree. They form intensive brown, blonde, violet and blue shades of high heat stability and fastness to light with a large number of the known developer substances. The compatibility of the compounds of the general formula I' with further couplers and direct dyestuffs is very good, and controlled modifications of the shades of known developer/coupler systems are therefore also possible. They can be prepared, according to the invention, economically and in a high purity and yield from the commercially obtainable precursors.

The new coupler compounds of the general formula I are therefore a valuable enrichment of the range of oxidation hair dyestuff precursors. Listed below in Table I are specific examples of compounds of Formula I. In Table I' are specific examples of compounds of Formula I'.

TABLE I

| The general formula I includes the following substituents: | |
|---|---|
| R | R$^1$ |
| H | —CH$_2$—CH$_2$—CH$_2$—OH |
| H | —CH$_2$—CH(CH$_3$)—OH |
| —CH$_2$—CH$_2$—OH | —CH$_2$—CH$_2$—OH |
| —CH$_2$—CH$_2$—OH | —CH$_2$—CH$_2$—CH$_2$—OH |
| —CH$_2$—CH$_2$—OH | —CH$_2$—CH(CH$_3$)—OH |
| —CH$_2$—CH$_2$—CH$_2$—OH | —CH$_2$—CH$_2$—CH$_2$—OH |
| —CH$_2$—CH$_2$—CH$_2$—OH | —CH$_2$—CH(CH$_3$)—OH |
| —CH$_2$—CH(CH$_3$)—OH | —CH$_2$—CH(CH$_3$)—OH |

TABLE I'

| The general formula I' includes the following substituents: | |
|---|---|
| R | R$^1$ |
| H | —CH$_2$—CH$_2$—OH |
| H | —CH$_2$—CH$_2$—CH$_2$—OH |
| H | —CH$_2$—CH(CH$_3$)—OH |
| —CH$_2$—CH$_2$—OH | —CH$_2$—CH$_2$—OH |
| —CH$_2$—CH$_2$—OH | —CH$_2$—CH$_2$—CH$_2$—OH |
| —CH$_2$—CH$_2$—OH | —CH$_2$—CH(CH$_3$)—OH |
| —CH$_2$—CH$_2$—CH$_2$—OH | —CH$_2$—CH$_2$—CH$_2$—OH |
| —CH$_2$—CH$_2$—CH$_2$—OH | —CH$_2$—CH(CH$_3$)—OH |
| —CH$_2$—CH(CH$_3$)—OH | —CH$_2$—CH(CH$_3$)—OH |

To prepare the compounds of the general formula I wherein R and R$^1$ represent a radical of the general formula Ia (—CH$_2$—CH(A)—B), the carbamates of the general formula II are treated with strong bases (alkali metal hydroxides or alkaline earth metal hydroxides), preferably with 10-50% strength sodium or potassium hydroxide solution. The carbamate of the formula II is initially introduced into the reaction vessel in water or an organic solvent (such as, for example, a (C$_1$–C$_4$)-alcohol, a water-miscible ether or mixtures thereof), and about 6 mol of alkali per mol of carbamate are then metered in at room temperature. It is also possible for the alkali, which can be diluted with the solvents mentioned, to be initially introduced into the reaction vessel and for the carbamate to be metered into the alkali in the pure form or as a solution in one of the organic solvents mentioned. In general any suitable inert organic solvent can be used. The mixture is then subsequently stirred for complete reaction, and if appropriate it can be heated under reflux. The reaction time is about 2 to 10 hours. To recover the desired product, the reaction solution, which has a pH of about 12-14, is neutralized to a pH of about 7 to 10 with an organic or inorganic acid; water is then added, if appropriate the solvents are distilled off, and the product is isolated.

The process will now be described for the preparation of the compounds of the general formula I'

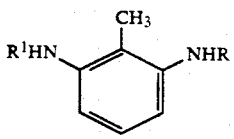

wherein R is a hydrogen atom and $R^1$ is a radical of the formula Ia

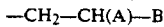     (Ia)

or R and $R^1$ are independent from each other and are represented by the formula Ia and if A in this formula represents a hydrogen atom, B is a hydroxyl group or HO—$CH_2$— group; or if A denotes a methyl group, B is a hydroxyl group.

Initially, in one embodiment, 2,6-diaminotoluene is introduced into the reaction vessel containing an inert organic solvent (such as, for example, dioxane, $C_1$- to $C_4$-alcohol, dimethylformamide, tetrahydrofuran, toluene, chlorobenzene, methyl ethyl ketone, ethylene glycol dimethyl ether or diethylene glycol dimethyl ether), and is heated up to a temperature between room temperature and the reflux temperature, preferably between 70° C. and the reflux temperature. Twice the molar amount of a chloroformic acid alkyl ester of the general formula Cl—COO—CH(X)—$CH_2$—Y (wherein X=H and Y=Cl; or X=$CH_3$ and Y=Cl; or X=H and Y=$CH_2Cl$) is then metered in. If appropriate, the solvents can be combined with water. An acid-binding agent can either be initially introduced at the same time or added in parallel with the chloroformic acid chloroalkyl ester already mentioned. Possible acid-binding agents are bases, such as alkali metal hydroxides, bicarbonates and carbonates; alkaline earth metal oxides, hydroxides, bicarbonates and carbonates; and tertiary organic amines. The reaction is complete after about 2-8 hours. For recovery of the product, it is possible either to add water and to stir the mixture until cold, or to filter off the inorganic salts and distil off some or all of the solvent.

Alternatively, in a second embodiment for carrying out the process for the preparation of the compounds of the general formula I' as defined above, 2-nitro-6-aminotoluene is used as the starting substance. In this embodiment, the 2-nitro-6-aminotoluene is reacted with one mol of chloroformic acid chloroalkyl ester of the general formula Cl—COO—CH(X)—$CH_2$—Y (wherein X=H and Y=Cl; or X=$CH_3$ and Y=Cl; or X=H and Y=$CH_2Cl$) in a solvent as mentioned above and under the conditions mentioned above. The carbamates of the general formula III thus obtained

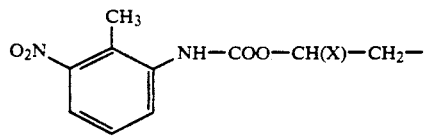

X=H, Y=Cl; X=$CH_3$, Y=Cl; or X=H, Y=$CH_2Cl$; are treated with strong bases (alkali metal hydroxides or alkaline earth metal hydroxides), preferably with 10-50% strength sodium or potassium hydroxide solution.

This treatment is carried out as follows: The carbamate of the formula III is initially introduced into the reaction vessel in water or an organic solvent (such as, for example, a ($C_1$-$C_4$)-alcohol, a water-miscible ether or mixtures thereof) and about 3 mol of alkali per mol of the carbamate are then added at room temperature. It is also possible for the alkali, which can be diluted with the solvents mentioned, to be initially introduced and for the carbamate to be metered into the alkali in the pure form or as a solution in one of the organic solvents mentioned. The mixture is then subsequently stirred for complete reaction, and if appropriate it can be heated under reflux. The reaction time is about 2 to 8 hours. For recovery of the desired product, the reaction solution, which has a pH of about 12-14, is neutralized to a pH of about 7 to 10 with an organic or inorganic acid; water is then added, if appropriate the solvents are distilled off, and the product is isolated.

The compounds of the general formula I' wherein R denotes a radical of the general formula Ia and $R^1$=H, or $R^1$ represents a radical of the general formula Ia and R=H, can be prepared by reduction of the compounds of the general formula IV with base metals or by catalytic reduction.

Customary catalysts, such as, for example, Raney nickel, palladium-on-active charcoal or platinum-on-active charcoal, are employed for catalytic reduction with hydrogen. The reaction temperature is between room temperature and 120° C., preferably between 40° and 80° C., and the pressure is between normal pressure and 100 bar, preferably between 20 and 80 bar. The solvents used are the customary solvents, such as water, toluene, glacial acetic acid, lower alcohols and ethers. When the reduction has been carried out and the catalyst has been removed, the product of the general formula I' can be isolated in the free form by stripping off the solvent under an inert gas. Preferably it is converted into a salt—also under an inert gas—by addition of approximately the equivalent amount of an acid. The salt formed is either precipitated directly or is obtained after stripping off the solvent. Suitable inorganic acids for the salt formation are, for example, hydrochloric acid and phosphoric acid, and suitable organic acids for the salt formation are, for example, acetic acid, propionic acid, lactic acid or citric acid.

The preparation process is illustrated by the following examples:

EXAMPLES

Example 1-Preparation of 2,6-bis(β-hydroxyethylamino)toluene

1st stage: Preparation of 2,6-bis(β-chloroethoxycarbonylamino)toluene

122 g of diaminotoluene and 105 g of calcium carbonate are initially introduced into 500 ml of monoethylene glycol dimethyl ether, and the mixture is heated to 78° C., while stirring. 300 g of β-chloroethylchloroformate are metered into the mixture in the course of 30 minutes, and the mixture is subsequently stirred at 80° C. for 3 hours. 500 g of ice and 500 g of water are then added to the mixture, and the product which has precipitated is filtered off, rinsed twice with 100 ml of water each time, and dried at 80° C. in a vacuum drying cabinet.

Yield: 301.5 g (90% of the theoretical yield).
Melting point: 148°-149° C.

2nd stage: Preparation of 2,6-bis(β-hydroxyethylamino)toluene

33.5 g of the 2,6-bis(β-chloroethoxycarbamoylamino)toluene obtained above under the 1st stage are initially introduced into the reaction vessel in 200 ml of water and 30 ml of methanol. The reaction mixture is heated to 75° C. and 70 g of 50% strength potassium hydroxide solution are added dropwise in the course of one hour. After the mixture has been subsequently stirred at 60° C. for 2½ hours, the pH is brought to 8.0 with glacial acetic acid and the reaction mixture is cooled slowly. The product which has precipitated is filtered off with suction, washed with water, and dried at 50° C. in a vacuum cabinet.

Yield: 18 g (86% of the theoretical value).
Melting point: 118°-120° C.

EXAMPLE 2

Preparation of 2,6-bis(γ-hydroxypropylamino)toluene

1st stage: Preparation of 2,6-bis(γ-chloropropyloxy-carbonylamino)toluene

61 g of 2,6-diaminotoluene and 52.5 g of calcium carbonate are reacted with 160 g of γ-chloropropylchloroformate in 250 ml of monoethylene glycol dimethyl ether under the conditions mentioned in Example 1, stage 1, and the mixture is worked up to recover the product.

172 g (95% of the theoretical value) of 2,6-bis(γ-chloropropyloxycarbonylamino)-toluene are obtained.

2nd stage: Preparation of 2,6-bis(β-hydroxypropylamino)-toluene

36.3 g of the 2,6-bis(γ-chloropropyloxycarbonylamino)-toluene prepared above under Example 2, stage 1, are reacted with 70 g of 50% strength aqueous potassium hydroxide solution in 190 ml of water and 40 ml of ethanol under the conditions mentioned in Example 1, stage 2, and the mixture is worked up.

19 g (80% of the theoretical yield) of 2,6-bis(γ-hydroxypropylamino)-toluene are obtained.

EXAMPLE 3

Preparation of 2-(β-hydroxyethylamino)-6-aminotoluene

1st stage: Preparation of β-chloroethyl N-(2-methyl-3-nitrophenyl)carbamate

91 g of 2-nitro-6-aminotoluene and 31 g of calcium carbonate are initially introduced into the reaction vessel in 750 ml of dioxane, and are heated up to 70° C. 87 g of β-chloroethyl chloroformate are added dropwise to this mixture in the course of two hours such that the reaction mixture refluxes gently, carbon dioxide being evolved. The mixture is subsequently stirred under reflux for a further two hours and then cooled to 35° C., and water and ice are added. The product which has precipitated is filtered off with suction, washed with water, and dried.

Yield: 152 g (98% of the theoretical value).
Melting point: 101°-103° C.

2nd stage: Preparation of 2-(β-hydroxyethylamino-6-nitrotoluene

25.8 g of the β-chloroethyl N-(2-methyl-3-nitrophenyl)-carbamate prepared under Example 3, stage 1, are initially introduced into the reaction vessel in 250 ml of water. The reaction mixture is heated to 80° C. and 35 g of 50% strength aqueous potassium hydroxide solution are then added in the course of one hour. After mixture has been subsequently stirred at 75° C. for 3 hours, its pH is brought to 8 with glacial acetic acid, and the reaction mixture is cooled slowly. The product which has precipitated is filtered off with suction, washed with water, and dried at 50° C. in a vacuum drying cabinet.

Yield: 16 g (82% of the theoretical value).
Melting point: 82°-83° C.

3rd stage: Preparation of 2-(β-hydroxyethylamino)-6-aminotoluene

10 g of the 2-(β-hydroxyethylamino)-6-nitro-toluene prepared under Example 3, stage 2 are transferred to a stainless steel autoclave together with 200 ml of methanol, about 2 g of Raney nickel are added, and catalytic reduction is carried out with hydrogen under a hydrogen pressure of 20 bar at 70° C. in the course of 6 hours. After the catalyst has been removed, the mother liquor is concentrated and the product is isolated and dried.

Yield: 7 g (85% of the theoretical yield).
Melting point: 97°-99° C.

The hair coloring agents according to the invention, which comprise the compounds of the general formula I' as couplei components and conventional developer substances generally known and used for oxidation hair dyeing, are distinguished by a good storage stability and, when used, produce very intensive color shades which range from dark blonde to blue and have good fastness properties, of the dyeings achieved with them.

When used in hair coloring agents, the coupler components are in general employed in approximately molar amounts based on the developer substances used. Although molar proportions prove to be advantageous, it is not a disadvantage if the coupler component is employed in a certain amount more or less than the molar amount.

The compounds of the general formula I, to be used according to the invention as coupler components, can be employed either as such or in the form of their salts with inorganic or organic acids (such as, for example, as chlorides, sulphates, phosphates, acetates, propionates, lactates or citrates).

The hair coloring agents according to the invention should comprise the new coupler substances of the general formula I' in a concentration of about 0.001 to 5.0% by weight, in particular 0.2 to 3.0% by weight.

Furthermore, it is not necessary for only one developer component to be used; it is also possible to use a mixture of different developer components.

Examples which may be mentioned of developer components to be employed are primary aromatic or heteroaromatic amines having another functional group in the p-position, such as p-phenylenediamine, p-toluylenediamine, p-aminophenol, N,N-dimethyl-p-phenylenediamine, chloro-p-phenylenediamine, methoxy-p-phenylenediamine, 2,5-diaminopyridine and its derivatives, and other compounds of the type mentioned, which additionally contain one or more functional groups (such as OH groups, $NH_2$ groups, NHR groups or NRR groups, wherein R represents an optionally substituted alkyl radical having 1 to 4 carbon atoms).

It is furthermore not necessary for only the coupler components of the general formula I' according to the invention to be used; rather, other coupler components which are already known and used, such as, for example, α-naphthol, 3,4-diaminobenzoic acid, resorcinol, 4-chlororesorcinol, m-aminophenol, m-phenylenediamine, m-toluylenediamine, 2,4-diaminoanisole, pyrocatechol, pyrogallol, 1,5- and 1,7-dihydroxynaphthalene, 5-amino-2-methylphenol, 6-amino-2-methylphenol and derivatives of the compounds mentioned, can also be employed in combination with the coupler of formula I' in order to achieve certain color shades.

The hair coloring agents moreover can comprise customary direct dyestuffs if this is necessary in order to achieve certain color shades. Oxidative coupling, that is to say development of the dyeing, can in principle be effected by atmospheric oxygen as is also the case with other oxidation dyestuffs. However, chemical oxidizing agents which are known in the art are advantageously employed.

The hair coloring agents according to the invention are aqueous agents; by this there are understood all agents which contain water in any manner, such as, for example, creams, emulsions, gels or also simple aqueous solutions. The compositions of the hair coloring agents represent a mixture of the dyestuff components with the additives customary for such cosmetics formulations.

Customary additives in solutions, creams, emulsions or gels are, for example, solvents, such as water, lower aliphatic alcohols, for example ethanol, propanol and isopropanol, or glycols, such as glycerol, and glycol ethers, such as propylene glycol; and furthermore wetting agents or emulsifiers from the classes of anionic, cationic, amphoteric or non-ionic surface-active substances, such as fatty alcohol sulphates, alkylsulphonates, alkylbenzenesulphonates, alkyltrimethylammonium salts, alkylbetaines, oxyethylated fatty alcohols, oxyethylated nonylphenols, fatty acid alkanolamides and oxyethylated fatty acid esters; and furthermore thickeners, such as, for example, higher fatty alcohols, starch, cellulose derivatives, petroleum jelly, paraffin oil and fatty acids.

The constituents mentioned are used in the amounts customary for such purposes; for example, the formulations can comprise the wetting agents and emulsifiers in concentrations of about 0.5 to 30% by weight, while they can comprise the thickeners in an amount of about 0.1 to 25% by weight.

The hair coloring agents according to the invention can be weakly acid, neutral or alkaline, depending on the composition. In particular, they have a pH in the alkaline range of between 7.5 and 11.5, the pH preferably being established with ammonia. However, it is also possible to use organic amines, for example monoethanolamine and triethanolamine, or inorganic bases, such as sodium hydroxide and potassium hydroxide.

In processes for oxidative dyeing of hair, the hair coloring agents of this invention, which comprise a combination of developer substances known in hair dyeing with at least one compound of the general formula I' as the coupler substance, and if appropriate additionally known coupler substances and direct dyestuffs, are mixed with an oxidizing agent shortly before use, and this mixture is applied to the hair. Possible oxidizing agents for development of the hair dyeing are chiefly hydrogen peroxide, for example as a 6% strength by weight aqueous solution, and addition compounds thereof on urea, melamine or sodium borate, as well as mixtures of such hydrogen peroxide addition compounds with potassium peroxodisulphate. The use temperatures here vary in the range from 15° to 40° C. After an action time of about 30 minutes, the hair coloring agent is removed by rising from the hair to be colored. Thereafter, the hair is subsequently washed with a mild shampoo and dried.

The following examples are intended to illustrate the subject matter of the invention in more detail, but without limiting it thereto.

EXAMPLE 4

Hair coloring agent in cream form

| |
|---|
| 1.00 g of 2,6-bis(2-hydroxyethylamino)toluene |
| 1.30 g of p-phenylenediamine HCl |
| 0.05 g of m-phenylenediamine |
| 2.00 g of oleic acid |
| 0.10 g of polyacrylic acid |
| 0.50 g of sodium dithionite |
| 4.00 g of lauryl alcohol diglycol ether sulphate, sodium salt (28% strength solution) |
| 15.0 g of cetyl alcohol |
| 8.00 g of ammonia, 25% |
| Water to 100 |

50 g of the above-mentioned hair coloring agent are mixed with 50 g of hydrogen peroxide solution (6% strength by weight) shortly before use. The mixture is allowed to act on medium-brown natural hair (having a 20% grey content) at 38° C. for 30 minutes. Thereafter, the hair coloring agent is rinsed out, and the hair is subsequently shampooed and dried. The hair has been given an intensive aubergine (eggplant) shade.

EXAMPLE 5

Hair coloring agent in cream form

| |
|---|
| 0.70 g of 2-β-hydroxyethylaminoamino-6-aminotoluene |
| 0.65 g of p-aminotoluene |
| 0.15 g of α-naphthol |
| 0.25 g of HC Red No. 3 |
| 2.10 g of oleic acid |
| 0.12 g of polyacrylic acid |
| 0.50 g of sodium sulphite, anhydrous |
| 4.50 g of lauryl alcohol diglycol ether sulphate, |

```
     sodium salt (28% strength solution)
16.0 g of cetyl alcohol
8.00 g of ammonia, 25%
     Water to 100
```

50 g of the above-mentioned hair coloring agent are mixed with 50 g of hydrogen peroxide solution (6% strength by weight) shortly before use. The mixture is allowed to act on dark blonde natural hair (having a 30% grey content) at 40° C. for 35 minutes. Thereafter, the hair coloring agent is rinsed out, and the hair is subsequently shampooed and dried. The hair has been given a strong red-violet shade.

EXAMPLE 6

Hair coloring agent in gel form

```
0.28 g of 2,6-bis(2-hydroxyethylamino)toluene
0.38 g of p-phenylenediamine HCl
0.03 g of α-naphthol
14.0 g of oleic acid
10.0 g of isopropanol
2.60 g of PEG 3-cocamine
10.0 g of ammonia, 25%
0.50 g of ascorbic acid
     Water to 100
```

40 g of the above-mentioned coloring agent are mixed with 60 g of hydrogen peroxide solution (6% strength by weight) shortly before use. The mixture is allowed to act on medium-blonde natural hair at 40° C. for 30 minutes. Thereafter, the hair coloring agent is rinsed out, and the hair is subsequently shampooed and dried. The hair has been colored an intensive rosewood shade.

EXAMPLE 7

Hair coloring agent in cream form

```
0.45 g of 2,6-bis(3-hydroxypropylamino)-toluene
0.45 g of p-phenylenediamine HCl
0.06 g of m-aminophenol
0.45 g of HC Red No. 3
2.00 g of oleic acid
0.10 g of polyacrylic acid
0.50 g of sodium sulphite, anyhdrous
4.00 g of lauryl alcohol diglycol ether sulphate,
        sodium salt (28% strength solution)
15.0 g of cetyl alcohol
8.00 g of ammonia, 25%
     Water to 100
```

50 g of the above-mentioned coloring agent are mixed with 50 g of hydrogen peroxide solution (6% strength by weight) shortly before use. The mixture is allowed to act on medium-blonde natural hair (having a 30% grey content) at 38° C. for 30 minutes. Thereafter, the hair coloring agent is rinsed out, and the hair is subsequently shampooed and dried. The hair has been given a strong red-violet shade.

Further variations and modifications of the invention will become apparent to those skilled in the art from the foregoing and are intended to be encompassed by the claims appended hereto.

German Priority Application P 41 32 615.6, filed Oct. 1, 1991, is relied on and incorporated by reference. U.S. Pat. No. 5,067,967, and U.S. patent application Ser. No. 07/746,415, filed Aug. 16, 1991, and which issued as U.S. Pat. No. 5,163,970, are incorporated by reference in their entirety.

What is claimed:

1. A composition for oxidative dyeing of hair, said composition comprising 0.001 to 5 percent by weight of the total composition of at least one diaminotoluene derivative of the formula I'

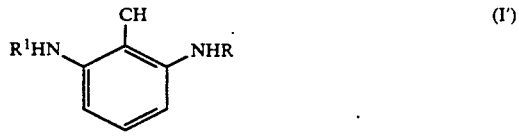

wherein R is a hydrogen atom and $R^1$ is a radical of the formula Ia $$-CH_2-CH(A)-B \qquad (Ia)$$

or R and $R^1$ are independent from each other and are represented by the formula Ia and if A in this formula represents a hydrogen atom, B is a hydroxyl group or HO—CH$_2$— group; or if A denotes a methyl group, B is a hydroxyl group; as the coupler component and a developer component selected from the group consisting of primary aromatic amines or heteroaromatic amines therewith.

2. The composition according to claim 1, wherein said coupler of formula I' is present in an amount of 0.2 to 3 percent by weight of the total composition.

3. The composition according to claim 1, characterized in that it comprises a further development and/or coupling component as dyestuff precursor.

4. The composition according to claim 1, further comprising a direct dyestuff.

5. The composition according to claim 1, wherein the pH of the composition is in the range from about 6.0 to 12.5.

6. The composition according to claim 5, wherein the pH of the composition is in the range from 7.5 to 11.5.

7. A component hair dyeing kit comprising (a) a developer selected from the group consisting of primary aromatic or heteroaromatic amines and a coupler and (b) oxidizing agent, wherein said coupler is present in an amount from 0.001 to 5 percent by weight of the total composition comprises at least one diaminotoluene derivative of the formula I':

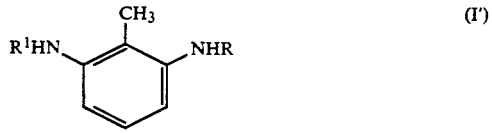

wherein R is a hydrogen atom and $R^1$ is a radical of the formula Ia $$-CH_2-CH(A)-B \qquad (Ia)$$

or R and $R^1$ are independent from each other and are represented by the formula Ia and if A in this formula represents a hydrogen atom, B is a hydroxyl group or HO—CH$_2$— group; or if A denotes a methyl group, B is a hydroxyl group.

8. A method for oxidative dyeing of hair, said method comprises (a) mixing the composition according to claim 1 with an oxidizing agent to form a mixture, and (b) applying said mixture to hair.

9. The method according to claim 8, wherein said oxidizing agent is hydrogen peroxide.

10. The method according to claim 9, wherein said hydrogen peroxide is a 6% strength by weight aqueous solution or addition compound thereof on urea, melamine or sodium borate or a mixture of said hydrogen peroxide addition compound with potassium peroxodisulphate.

11. A method for the use or a compound of the formula I'

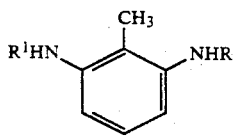

(I')

wherein R is a hydrogen atom and $R^1$ is a radical of the formula Ia

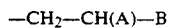

$-CH_2-CH(A)-B$ (Ia)

or R and $R^1$ are independent from each other and are represented by the formula Ia and if A in this formula represents a hydrogen atom, B is a hydroxyl group or HO—CH$_2$— group; or if A denotes a methyl group, B is a hydroxyl group; as a coupler in a hair dyeing kit comprising (a) a developer selected from the group consisting of primary aromatic amines and heteroaromatic amines and a coupler and (b) oxidizing agent, wherein said coupler is present in an amount of 0.001 to 5 percent by weight of the total composition and comprises at least one diaminotoluene derivative of the formula I'.

12. A cream for oxidative dyeing of hair, said cream comprising an emulsifier, a thickener, and 0.001 to 5 percent by weight of the total composition of at least one diaminotoluene derivative of the formula I'

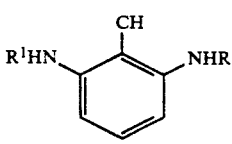

(I')

wherein R is a hydrogen atom and $R^1$ is a radical of the formula Ia

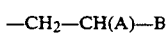

$-CH_2-CH(A)-B$ (Ia)

or R and $R^1$ are independent from each other and are represented by the formula Ia and if A in formula Ia represents a hydrogen, B is a hydroxyl group or HO—CH$_2$— group; or if A denotes a methyl group, B is a hydroxyl group; as the coupler component and a developer component selected from the group consisting of primary aromatic amines and heteroaromatic amines therewith.

* * * * *